United States Patent [19]

Hodge et al.

[11] Patent Number: 4,915,132

[45] Date of Patent: Apr. 10, 1990

[54] GAS REGULATOR SELECTOR VALVE

[75] Inventors: Colin G. Hodge, Columbia, Md.; Douglas D. Carden, Barneveld, Wis.

[73] Assignee: The BOC Group, Inc., New Providence, N.J.

[21] Appl. No.: 300,662

[22] Filed: Jan. 23, 1989

[51] Int. Cl.⁴ ............................................. F16K 11/08
[52] U.S. Cl. .......................... 137/625.41; 128/205.24; 137/599; 137/625.46; 251/297; 251/317; 251/368
[58] Field of Search ............... 251/297, 312, 304, 317, 251/368; 128/205.19, 205.24; 137/625.41, 599, 625.46

[56] References Cited

U.S. PATENT DOCUMENTS

| | | | |
|---|---|---|---|
| 756,491 | 4/1904 | Gold | 251/297 X |
| 1,244,630 | 10/1917 | Mitchell | 251/297 X |
| 3,048,192 | 8/1962 | Murphy | 251/297 X |
| 3,115,896 | 12/1963 | Roberts et al. | 251/297 X |
| 3,837,360 | 9/1974 | Bubula | 251/297 X |
| 3,957,082 | 5/1976 | Fuson et al. | 137/625.41 |
| 4,742,848 | 5/1988 | Black | 251/297 X |

FOREIGN PATENT DOCUMENTS 1902 of 1915 United Kingdom ........... 128/205.24

Primary Examiner—Stephen M. Hepperle
Attorney, Agent, or Firm—Roger M. Rathbun; Larry R. Cassett

[57] ABSTRACT

A selector valve for use with a hospital vacuum on position in pressure module to supply vacuum or pressure to a utilization means. The selector valve has two or more positions and includes a positive stop at each of its positions through the use of molded plastic parts that interact together to eliminate springs or other components that are tedious to assemble. The entire selector valve is comprised of a minimum of parts and costly lapped surfaces are eliminated by molding a gasket material to one of the components of the valve. The overall multiposition selector valve is thus inexpensive to manufacture by utilizing a minimal number of plastic molded parts and that are easy to assemble.

17 Claims, 5 Drawing Sheets

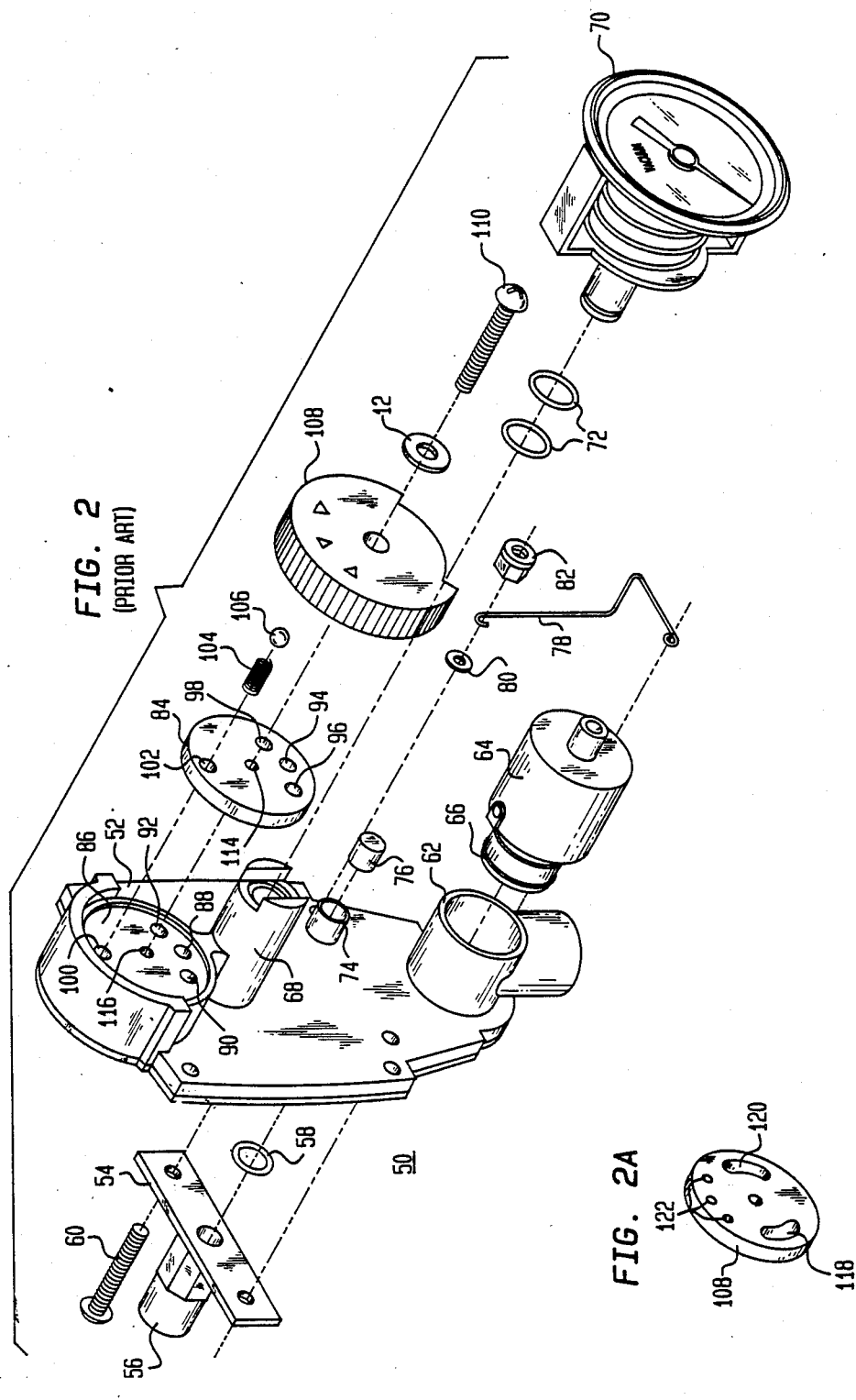

GAS REGULATOR SELECTOR VALVE

BACKGROUND OF THE INVENTION

This invention relates to a medical gas or vacuum regulator used to provide gas or vacuum for patient use, and, more specifically, it relates to an improved selector valve that has a plurality of positions with means to hold the valve in each of such positions and which overall is made up of fewer parts involving less tedious assembly than prior selector valves.

In medical applications, vacuum is often used for various suctioning functions carried out on a patient to remove fluids and in hospitals, there typically is provided, a central vacuum system where the various pieces of suction equipment may be connected by plug in receptacles, to that system.

In order to control the level of vacuum, modules are generally utilized and which may connect directly into the vacuum system and which include a pressure regulator, a gauge to determine the vacuum level and a selector valve that allows the operator to select either unregulated vacuum directly from the hospital central system or, alternatively, vacuum that has been regulated by use of the regulator incorporated into the module.

Due to increasing competition in the production of such modules, it is becoming significant to reduce, to the extent possible, the cost of such modules in order to maintain competitiveness. Since one of the main components of such modules is the multiposition selector valve, reduction in its cost is important, both from a materials as well as an assembly time standpoint.

Present selector valves used for the aforementioned purpose generally have a number of parts and require certain tedious assembly. As an example, one device currently on the market includes a rotatable valve where the valve surfaces require critical flatness to the extent that one of the rotating surfaces of the moving valve member must be lapped surface steel, thus the parts are fairly expensive.

In addition, it is desirable that a position latch be provided in each position so that the operator knows when the selector valve is fully in one of the selected positions, thus a spring and detent system is used to give the positive feel to the valve. Assembly of spring and detent types of positive valve engagement are, however, tedious to assemble since the assembler must manually align a tiny spring and spring follower in order to complete the unit.

SUMMARY OF THE INVENTION

In the present invention, a gas regulator selector valve is provided having four individual parts and all of which are easily assembled without any tedious steps being performed.

Specifically the selector valve comprises only three molded plastic parts that are assembled with a single securing means, such as a screw, and no additional seals are required to be aligned, no small parts, such as springs that require special attention by the operator and thus the overall cost of material as well as assembly is relatively low.

The selector valve has positive stops at each of its positions by one or more projections molded in to one of the main components and which are, by the particular mold, biased toward a specially shaped detent or detents that lock the valve into each of its positions.

Thus the positive locking feature is accomplished by a specially molded component rather than the assembly of any separate part, such as springs.

The selector valve also does away with various individual seals or lapped surfaces by molding a gasket material directly to one of the valve surfaces, again, reducing cost of the overall module.

BRIEF DESCRIPTION OF THE DRAWINGS

FIG. 2 is an exploded view of a prior art gas regulator module illustrating the components thereof;

FIG. 2A is a perspective view of one of the individual components of the gas regulator module of FIG. 2;

DETAILED DESCRIPTION OF THE PREFERRED EMBODIMENT

Figure 1:
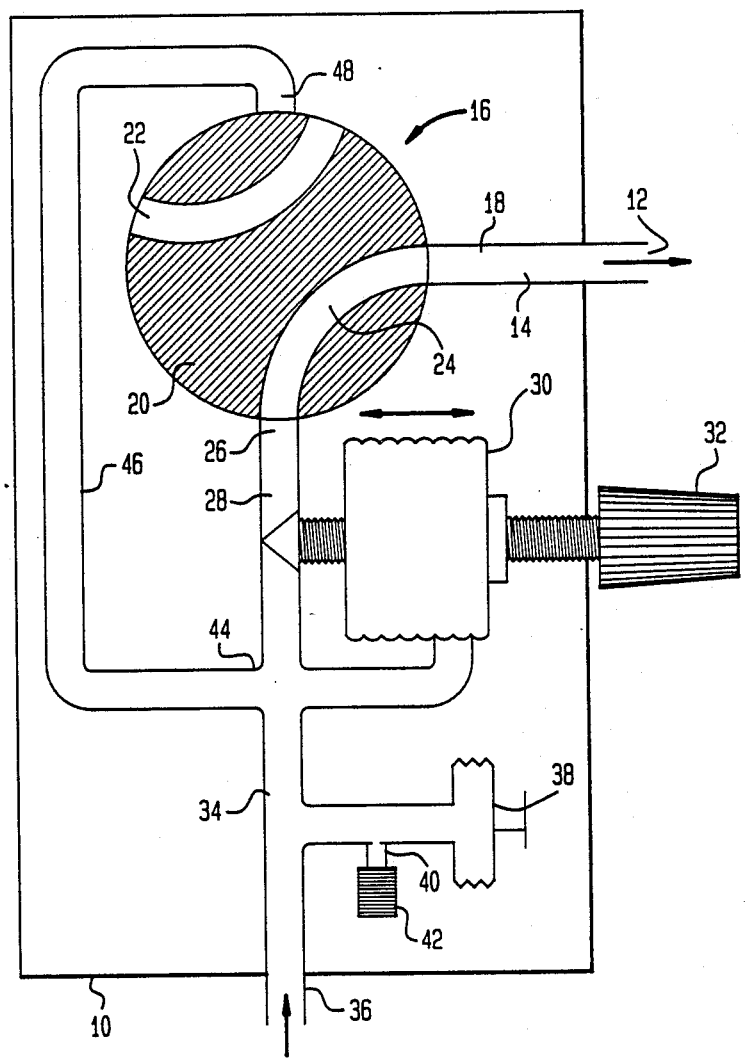
FIG. 1 is a schematic view of the flow path and components used in a typical gas regulator module used for medical applications.

Turning first to FIG. 1, there is shown a schematic of a typical vacuum control module utilized in a hospital environment. As described herein, the invention will be illustrated as applying to the providing of vacuum for use on a patient, however, it will be understood that the selector valve may readily be used with positive pressure applications as well. Also, the preferred embodiment described is a three position selector valve, however, the invention is applicable to any multiposition selector valves. Also, in accordance with convention, the direction of flow will be used to differentiate an inlet and an outlet, thus, when the vacuum module is described, it's delivery port to an end use device will be designated as an inlet since actual flow is into the module from the particular device. Obviously, when a pressure module is being used, that same delivery port is referred to as the outlet of the module since flow is then from the module toward the end use device.

The vacuum control module 10 comprises a vacuum module outlet 12 that connects to a source of vacuum, in most cases, a central vacuum system piped to various rooms of a hospital. The vacuum level from such system, while relatively constant, is basically unregulated and may be at a negative pressure of between about 300 and 600 mmHg gauge.

The vacuum seen by vacuum module outlet 12 is transmitted by means of passageway 14 within the vacuum control module 10 into vacuum selector valve 16 through a valve outlet 18. Within vacuum selector valve 16 is a rotatable valve operator 20 having formed therein two passages 22 and 24.

As shown in the position of FIG. 1, passage 24 connects valve outlet 18 with valve inlet 26, thus in the position shown, vacuum from vacuum module outlet 12 is communicated through vacuum selector valve 16 to valve inlet 26. A further passageway 28 transmits the vacuum from valve inlet 26 and a regulator 30 having an external knob 32 is present in passageway 28 in order to adjust and maintain a desired level of vacuum that thereafter is transmitted via passageway 34 to the vacuum module inlet 36 which is thereafter available to an end use device such as a suction line for withdrawing fluids from a patient.

Also communicating with passageway 34 is a vacuum gauge 38 where vacuum delivered to, for example, the patient can be read and which may include a bleed hole 40 with a filter 42 to return the gauge to a zero reading when the vacuum is disengaged A tee 44 joins passageway 34 to a further passageway 46 leading to valve outlet 48. As can be seen in the FIG. 1 position, valve outlet 48 is blocked by rotatable valve operator 20 and thus no vacuum is transmitted to passageway 46.

In the FIG. 1 position of rotatable valve operator 20, therefore, the line vacuum from the central vacuum system present at vacuum module outlet 12 is transmitted through passage 24 in rotatable valve operator 20 and passes via passageway 28 and passageway 34 to vacuum module inlet 36 where it is available to an end use on a patient. Since regulator 30 controls the level of vacuum present at vacuum module inlet 36 through passageway 28, the vacuum module inlet 36 provides a controllable regulated vacuum level that can be set by an operator and monitored by viewing the vacuum gauge 38.

Figure 1A:
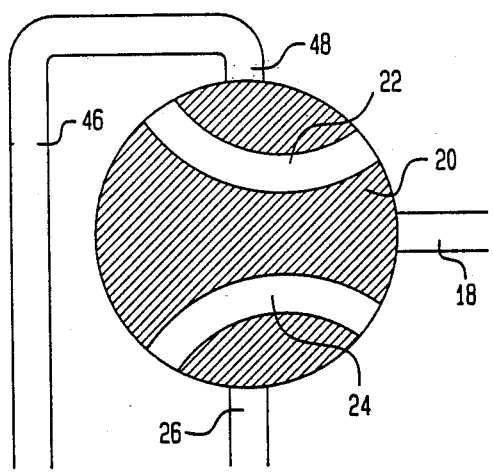
FIG. 1A and 1B are schematic views of the selector valve portion of the module of FIG. 1 showing that valve in its alternate positions.
Figure 1B:
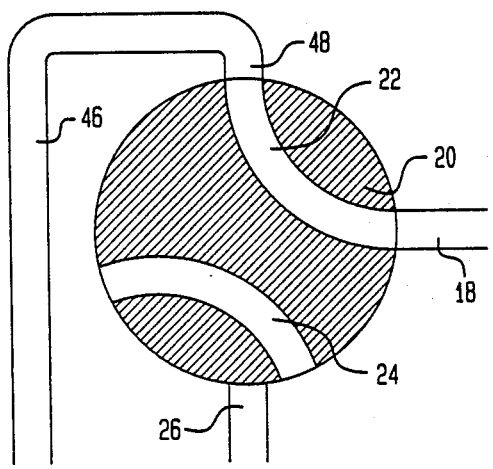

Turning to FIGS. 1A and 1B, there is shown a schematic view of two other positions of rotatable valve operator 20. In FIG. 1A, the rotatable valve operator 20 is in its off position such that the valve outlet 18 is blocked. No vacuum can be transmitted from the vacuum source and therefore the overall vacuum control module 10 is in its fully off position.

In FIG. 1B, the valve operator 20 is in alignment with valve inlet 48 and valve outlet 18, thus, in this position, unregulated vacuum is communicated from the valve outlet 18 to the valve inlet 48 and thus to passageway 46. As seen by FIG. 1, therefore, the vacuum in passageway 46 is transmitted directly to vacuum module inlet 36 where it is available for use by an end user in an unregulated form.

Accordingly, it may be seen that the rotatable valve operator 20 may be moved between three positions, one of which provides unregulated vacuum to vacuum module inlet 36, another of which provides regulated vacuum to vacuum module inlet 36 and another of which is an off position where no vacuum is present at the valve module inlet 36.

Thus the operator may conveniently select the vacuum to the patient by choosing regulated vacuum, unregulated vacuum or turn the module to the off position.

In FIG. 2, there is shown an exploded view of a typical prior art vacuum control module 50 and which includes, as its main component, a back body 52. Back body 52 contains various passageways for connecting to the various features to be explained herein, however, the passageways are conventional and are therefore not shown in the FIG. Other conventional features include an outlet connector 54 which is affixed to the rear face of back body 52 and which includes an rearwardly projecting outlet 56 for connection to the central supply of vacuum in the hospital An O-ring 58 insures a gas tight connection between outlet connector 54 and the corresponding passageway within back body 52. Outlet connector 54 is connected to back body 52 by means such as screws 60, only one of which is shown.

Forwardly projecting from back body 52 is a cylindrical hollow flange 62 into which is fitted a regulator assembly 64 and is sealed therein by O-rings 66.

A further forwardly projecting hollow flange 68 is provided integrally molded with back body 52 and into which is fitted a gauge assembly 70 for displaying the level of vacuum. Again, O-rings 72 are utilized to provide the necessary sealing of gauge assembly 70 within the hollow flange 68.

Other features include a bleed outlet 74 into which is fitted a filter 76 and a conductivity link 78 is affixed to the front face of back body 52 by means of washer 80 and nut 82.

Finally, the selector valve of the vacuum control module 50 is comprised of a selector plate 84 that has one face thereof sealed by a double sided adhesive gasket to a forward face 86 of the back body 52. The forward face 86 has a plurality of ports, an outlet port 88 and two inlet ports 90, 92 radially oriented with respect to outlet port 88. Those ports 88, 90 and 92 extend into the passageways within back body 52 in a manner shown by the schematic of FIG. 1, that is, inlet port 92 delivers a source of unregulated vacuum and inlet port 90 conveys a source of regulated vacuum. Selector plate 84, when sealed to forward face 86 has corresponding apertures 94, 96 and 98 which align, respectively with outlet port 88 and inlet ports 90 and 92. A further bored hole 100 in forward face 86 and corresponding aperture 102 in selector plate 84 are provided and, upon assembly, a spring 104 is fitted within bored hole 100 and extends through aperture 102. A small ball 106 is then positioned on the free end of the spring 104.

A selector dial 108 is rotatably affixed to the back body 52 by means such as screw 110, washer 112 passing through aperture 114 in selector plate 84 and engaging a threaded hole 116 in the back body 52. As such, the lapped seal face of selector dial 108 fits flush against the outer face of selector plate 84 and forms a seal thereagainst.

In order for the respective mating faces of selector plate 84 and selector dial 108 to form a seal, the selector plate 84 must be perfectly flat and, accordingly, it is constructed of steel and its mating face is lapped. The mating face of selector dial 108 is likewise flat, and lapped, however the selector dial 108 may be injection molded plastic, such as acrylic.

As shown in FIG. 2A, which is a perspective view of the mating face of selector dial 108, a pair of kidney shaped recesses 118 and 120 are formed and which selectively allow the communication of vacuum between the various ports. In addition, three detents 122 are formed in the mating face of selector dial 108.

As can now be seen, in FIG. 2, when assembled, the selector dial 108 can be moved between each of three positions, one, for example, when the selector dial 108 is twisted clockwise moving kidney shaped recess 118 into position spanning outlet port 88 and inlet port 92 thereby allowing unregulated vacuum at outlet port 88 to be communicated to inlet port 92 and thence to the user. In another position the selector dial 108 is twisted counterclockwise, such that the kidney shaped recess 120 is moved into position spanning outlet port 88 and outlet port 90 whereby regulated vacuum is provided to the patient.

In the center position of selector dial 108, the outlet port 88 is closed and thus no vacuum is present from the vacuum control module 50.

The spring 104 and ball 106 interact with selector dial 108 at each of the aforedescribed positions to provide a positive stop at each position. Specifically, at each of the three positions, one of the detents 122 is in alignment with bored hole 100 such that the spring 104 forces ball 106 to fit within that detent. As noted, the three detents 122 therefore align with the three positions of selector dial 108 and at each such position, the ball 106 is biased into one of the corresponding detents 122 to hold the selector dial 108 in the desired position.

Accordingly, the vacuum control module carries out its intended purpose but its manufacture, including assembly, is somewhat difficult. The selector plate 84 must be a lapped steel finish to accomplish a sufficient seal against selector dial 108. Likewise, the selector dial must have a lapped face. In addition, a double sided adhesive, nonporous gasket is required on the side of selector plate 84 facing forward face 86. The positive stop feature necessitates rather tedious manual assembly of a spring and ball, not only for assembly but disassembly for cleaning or repair.

Figure 3:
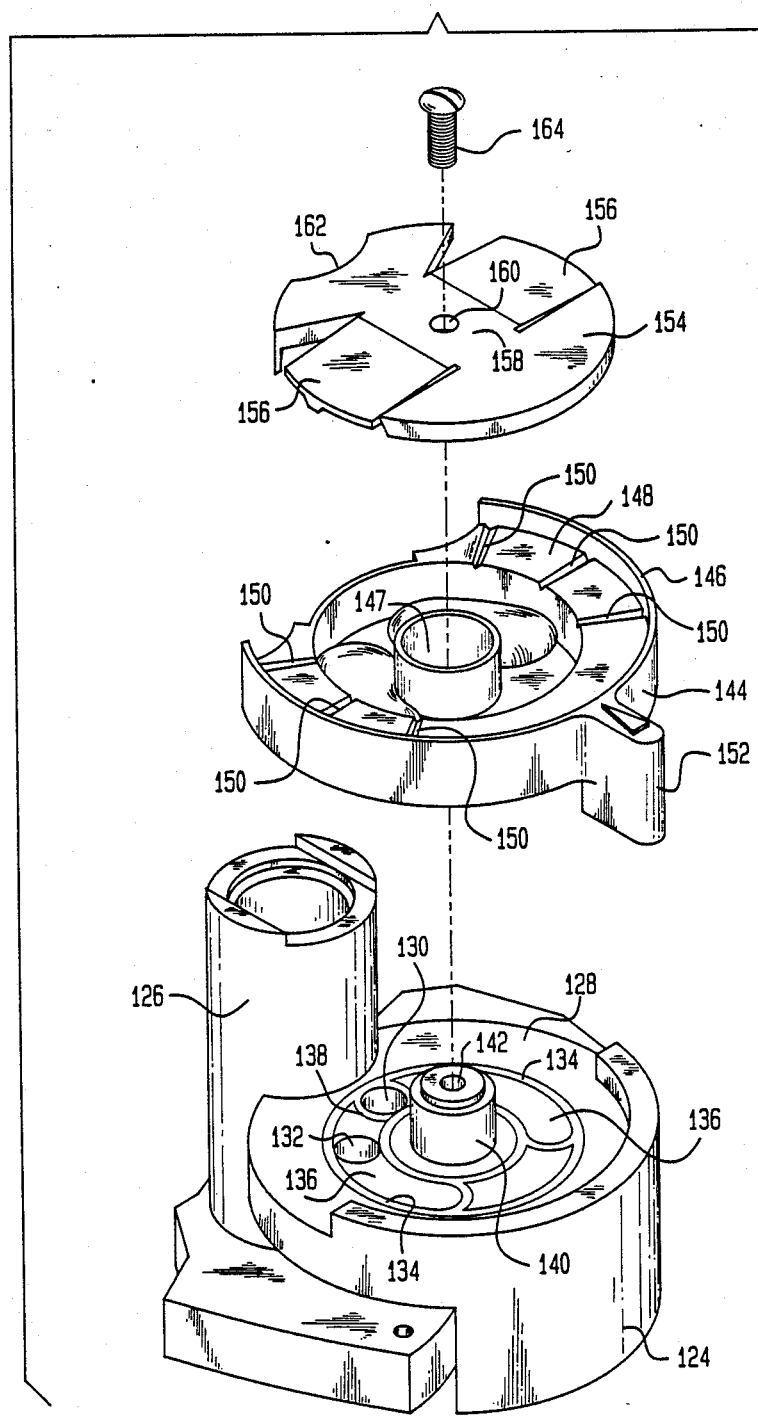
FIG. 3 is an exploded view of the components of the selector valve of the present invention.

Turning now to FIG. 3, there is shown an exploded view of the selector valve constructed in accordance with the present invention. The view is broken away to illustrate only the selector valve portion of a vacuum regulator module, the remaining portions being similiar to the prior art device illustrated in FIGS. 2 and 2A. The gas regulator body 124 is one of the components making up the selector valve and, again, includes various passageways and manifolding to transmit the vacuum signal to the desired ports of the overall module. Gas regulator body 124 has an outwardly projecting hollow flange 126 for receiving a gauge assembly (not shown). Adjacent the hollow flange 126 is formed a circular flat face 128 on gas regulator body 124 in which are formed three ports, specifically an outlet port 130 and an inlet port 132. A second inlet port is located, but not shown in FIG. 3, opposite of the inlet port 132 from outlet port 130 and generally at the same radial location. A raised ridge 134 of a general kidney shape is formed on the flat face 128 leaving an indented surface 136 within the raised ridge 134. In addition, a circular ridge 138 surrounds outlet port 130.

A cylindrical post 140 depends outwardly from the center of circular flat face 128 and has a hole 142 in its center.

In general, gas regulator body 124 may be made of high impact molded plastic, and one suitable composition is a ABS plastic (Acrylonitrile - butadiene - styrene).

A selector dial 144 overlies the circular flat face 128 and has an outer circular flange 146 that encompasses a predetermined portion of the perimeter of selector dial 144. A central opening 147 is formed in selector dial 144 of a predetermined diameter so as to fit over cylindrical post 140 and rotate thereabout with a reasonably close tolerance fit. The selector dial 144 has two faces, one of which faces inwardly and fits tightly against the circular flat face 128 of gas regulator body 124 and, when assembled, forms a seal thereagainst. The other, outward face 148 with respect to gas regulator body 124 has a plurality of detents 150 formed thereon. As shown, the detents 150 are radially oriented eminating outwardly from the center of the selector dial 144. Detents 150 are also formed in the outward face 148 such that they increase in depth into outward face 148 with increasing radius length away from the center of selector dial 144 and increase in width in the same manner with increasing radius.

In summary, each detent 150 is formed along a predetermined radius having the center of selector dial 144 as its center and is formed in outward face 148 as to increase in both depth and width as the detent 150 increases in radius length. A tab 152 extends from circular flange 146 for easy grip by an operator. As will become clear, selector dial 144 is injection molded of a material that can adhere to a gasket material and typical of materials for the selector dial 144 are polyethylene or polypropylene.

A pair of flexible arms 156 depend outwardly from the central hub 158 of switch plate 154 and a center hole 160 is formed therein. An indentation 162 is formed in the outer periphery of switch plate 154 and which fits against hollow flange 126 and thereby hold switch plate 154 from rotational movement by the selector dial 144 when the unit is assembled. The assembly is completed by means of self topping screw 164 that passes through center hole 160 and is screwed into hole 142.

Figure 4:
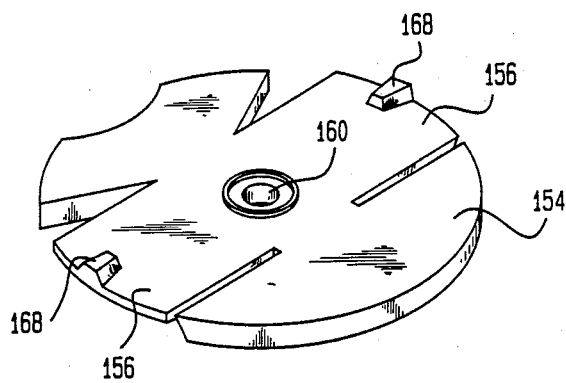
FIG. 4 is a perspective view of the switch plate component of the present invention and illustrating the projection means.

Turning now to FIG. 4, there is shown a perspective view of the switch plate 154 used with the present invention and illustrating the inward face 166 thereof that mates with the outward face 148 of selector dial 144. As may be seen, the switch plate 154 is a one-piece molded plastic construction having the plurality of flexible arms 156 and on each flexible arm 156 there is formed a projection 168. As can be seen, projection 168 are the mirror images of detents 150 of the selector dial 144 (FIG. 3).

Projections 168 are formed in the shape of wedges aligned on radii form the center of center hole 160 and increase in width as well as thickness as the distance from the center along the radius increases. Thus, when the switch plate 154 is assembled atop selector dial 144 in accordance with FIG. 3, the projections 168 fit within the detents 150 to hold the position of selector dial 144 in a selected position. The projections 168 are biased into those detents 150 by the geometry and material of switch plate 154 with its flexible arms 156, thus positive positions are retained without springs or other small parts requiring tedious assembly.

Figure 5:
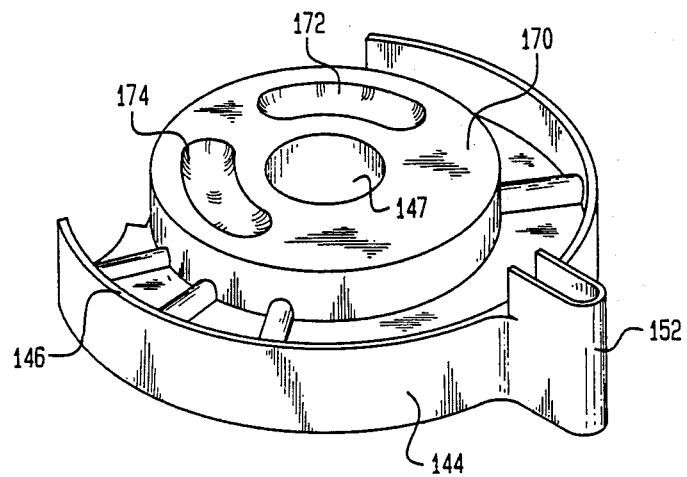
FIG. 5 is a perspective view of the selector dial component of the present invention illustrating its sealing surface.

Turning finally to FIG. 5, there is shown a perspective view of the selector dial 144 used with the instant invention and illustrating the inward face 170 thereof. Inward face 170 has molded thereon, a gasket material such as styrene-ethylene/butylene-styrene copolymer thermoplastic elastomer, it being important to note that such material may be readily molded directly to materials such as polyethylene and polypropylene and is the reason those materials are preferred for molding the selector dial 144. Other materials, however, may be used.

A pair of kidney shaped recesses 172 and 174 are formed in the inward face 170 of selector dial 144 and as can readily be seen in FIG. 3, serve to selectively channel vacuum from the vacuum outlet port 130 to one of the two inlet ports 132. Selector dial 144 is thus moveable between each of three positions in the same manner as described with respect to the prior art device of FIG. 2 and the schematics of FIG. 1, 1A and 1B.

In the present invention, however, the gasket material formed on the inward face 170 of selector dial 144 acts directly against outward flat face 128 of gas regulator body 124 and forms a seal thereagainst without the need for steel or plastic mating lapped surfaces. In addition, the use of the raised ridge 134 and circular ridge 138 assist in providing a seal yet allow selector dial 144 to be easily moved since actual contact is between those ridges 134 and 138 with the gasket material on inward face 170, thus friction is relatively low and there is little drag inhibiting rotation of selector dial 144, yet the seal is effective.

As may also now be seen FIGS. 3–5, the selector dial 144 is but a one piece molded part overlying the gas regulator body 124 and performs the valve function as well as cooperated with the one piece molded switch plate 154 in providing positive position stops. The entire unit is easily assembled by a screw 164.

Therefore, there are a minimum number of relatively inexpensive molded parts, assembled without tedious steps by the assembler and, accordingly, less costly to produce in terms of both component costs and assembly costs.

What is claimed:

1. A gas regulator selector valve, said selector valve comprising a regulator body having a vacuum outlet port adapted to be connected to an end utilization means of vacuum and at least one inlet port, a selector dial affixed to said regulator block and having one face thereof overlying said ports, said one face of said selector dial having a sealing material affixed thereto and having at least one recess formed therein, said selector dial being moveable between a first position wherein said at least one recess overlies and allows communication between said vacuum outlet port and said at least one inlet port, and at least a second position wherein said vacuum outlet port is blocked, said selector dial having a plurality of detents formed in the other face thereof with at least one detent corresponding to each of said at least two positions, and a switch plate affixed to said regulator body contacting said other face of said selector dial, said switch plate body having at least one flexible arm including a projection generally shaped to fit within said plurality of detents, said projection being biased toward said other face by said flexible arm to cause said projection to enter a corresponding detent in each of said at least two positions to hold said selector dial in one of said at least two positions.

2. A gas regulator selector valve as defined in claim 1 wherein said selector dial is rotatable about a center point and said vacuum outlet port and said at least one inlet port have centers on about the same radii from said center point.

3. A gas regulator selector valve as defined in claim 2 wherein said at least one recess is kidney shaped having an arc with a centerline aligned with the centers of said vacuum outlet port and said at least one inlet port.

4. A gas regulator selector valve as defined in claim 2 wherein said detents are formed along a predetermined radius from said center point and increase in width as the length of said radius increases from said center point.

5. A gas regulator selector valve as defined in claim 4 wherein said detents increase in depth as the length of said radius increases from said center point.

6. A gas regulator selector valve as defined in claim 5 wherein said projection is molded with said switch plate and is shaped as a mirror image to said detents.

7. A gas regulator selector valve is defined in claim 2 wherein said sealing material is injected molded to said selector dial.

8. A gas regulator selector valve as defined in claim 7 wherein said sealing material is styrene-ethylene butylene-styrene copolymer thermoplastic elastomer and said selector dial is polyethylene or polypropylene.

9. A gas regulator selector valve, said selector valve comprising a gas regulator body having a vacuum outlet port adapted to be connected to an end utilization means of vacuum and two inlet ports, a selector dial affixed to said regulator block and having one face thereof overlying said ports, said one face of said selector dial having a sealing material affixed thereto and having a pair of generally kidney shaped recesses formed therein, said selector dial being rotatable between a first position wherein one of said kidney shaped recesses overlies and allows communication between said outlet port and one of said inlet ports; a second position wherein said outlet port is blocked, and a third position wherein said other kidney shaped recess overlies and allows communication between said outlet port and the other of said inlet ports, said selector dial having a plurality of detents formed in the other face thereof corresponding to each of said three positions, and a switch plate covering said other face of said selector dial, said switch plate affixed to said regulator block and having at least one flexible arm having a projection generally shaped to fit within said plurality of detents, said projection biased toward said other face by said at least one flexible arm to cause said projection to enter a corresponding detent in each of said three positions to hold said selector dial in one of said three positions.

10. A gas regulator valve as defined in claim 9 wherein said selector dial is rotatable about a center point and said inlet ports and said vacuum outlet port are located on approximately equal radii from said center point.

11. A gas regulator valve as defined in claim 10 wherein said outlet port is located approximately midway between said inlet ports and sad pair of kidney shaped recesses have arcs with centerlines generally in alignment with the centers of said inlet ports and said outlet port and located at approximately the same radius from the center point of said selector dial.

12. A gas regulator selector valve as defined in claim 11 wherein said detents are formed along a predetermined radius from said center point and increase in width as the length of said radius increases from said center point.

13. A gas regulator selector valve as defined in claim 12 wherein said detents increase in depth as the length of said radius increases from said center point.

14. A gas regulator selector valve as defined in claim 11 wherein said switch plate is a single piece injection molded plastic part having said projections formed at or near the end of flexible arms radially extending from the center of said switch plate.

15. A gas regulator selector valve as defined in claim 9 wherein said sealing material is injection molded to said selector dial.

16. A gas regulator selector valve as defined in claim 15 wherein said sealing material is styrene-ethylene butylene-styrene copolymer thermoplastic elastomer and said selector dial is polyethylene or polypropylene.

17. A gas regulator selector valve, said selector valve comprising a regulator body having an outlet port adapted to deliver a gas under pressure to an end utilization and at least one inlet port, a selector dial affixed to said regulator block and having one face thereof overlying said ports, said one face of said selector dial having a sealing material affixed thereto and having at least one recess formed therein, said selector dial being moveable between a first position wherein said at least one recess overlies and allows communication between said pressure outlet port and said at least one inlet port, and at least a second position wherein said pressure outlet port is blocked, said selector dial having a plurality of detents formed in the other face thereof with at least one detent corresponding to each of said at least two positions, and a switch plate affixed to said regulator body contacting said other face of said selector dial, said switch plate body having at least one flexible arm including a projection generally shaped to fit within said plurality of detents, said projection being biased toward said other face by said flexible arm to cause said projection to enter a corresponding detent in each of said at least two positions to hold said selector dial in one of said at least two positions.

* * * * *